United States Patent
Watanabe et al.

(10) Patent No.: US 6,692,241 B2
(45) Date of Patent: Feb. 17, 2004

(54) INFUSION PUMP

(75) Inventors: Takashi Watanabe, Fuji (JP); Masaru Nakanishi, Fuji (JP)

(73) Assignee: Terumo Kabushiki Kaisha, Shibuya-Ku (JP)

( * ) Notice: Subject to any disclaimer, the term of this patent is extended or adjusted under 35 U.S.C. 154(b) by 273 days.

(21) Appl. No.: 09/920,717

(22) Filed: Aug. 3, 2001

(65) Prior Publication Data

US 2002/0019612 A1 Feb. 14, 2002

(30) Foreign Application Priority Data

Aug. 14, 2000 (JP) ........................................ 2000-245956

(51) Int. Cl.[7] .............................................. F04B 43/08
(52) U.S. Cl. ................................ 417/477.2; 417/477.9; 604/153
(58) Field of Search ........................... 417/477.2, 477.9, 417/477.11, 479; 604/153

(56) References Cited

U.S. PATENT DOCUMENTS

| | | | |
|---|---|---|---|
| 4,493,706 A | * | 1/1985 | Borsanyi et al. ............ 604/153 |
| 4,689,043 A | | 8/1987 | Bisha |
| 5,090,877 A | | 2/1992 | D'Silva |
| 5,290,158 A | | 3/1994 | Okada |
| 5,868,712 A | * | 2/1999 | Briggs et al. ................ 604/153 |
| 5,988,983 A | | 11/1999 | Furusawa |
| 6,056,522 A | | 5/2000 | Johnson |
| 6,261,262 B1 | * | 7/2001 | Briggs et al. ................ 604/153 |

FOREIGN PATENT DOCUMENTS

EP      0 881 388 A1      12/1998

* cited by examiner

*Primary Examiner*—Charles G. Freay
(74) *Attorney, Agent, or Firm*—Burns, Doane, Swecker & Mathis, LLP (57) ABSTRACT

When a door is opened, a midway part of an infusion tube is temporarily held in a fixed position of a pump body and the door is to be closed, in order to actively prevent the door from being closed if the infusion tube is not properly set in its fixed position, so that a back plate base 132 can be placed in a state of interposition in which the infusion tube is properly held and an immovable state in relation to the door 4 can be ensured, there are provided a stopper member 70 to be shifted in the direction of arrow d1 by a shift energizing force to be placed in a state of engagement with the back plate base 132 when the door is open and a shape 64 provided on the pump body for shifting the stopper member 70 so as to eliminate the state of engagement when the infusion tube 2 is properly held temporarily in said fixed position and the door is shifted to a closed state in relation to the pump body 3.

4 Claims, 10 Drawing Sheets

DOOR IS FULLY CLOSED

DOOR IS FULLY CLOSED

FIG. 8B

DOOR IS FULLY OPEN

DOOR IS FULLY CLOSED

FIG. 10

INFUSION PUMP

FIELD OF THE INVENTION

The present invention relates to an infusion pump, and more particularly to an infusion pump having a function to prevent, when a door is opened and a midway part of a detachable infusion tube is to be temporarily held in a fixed position of a pump body, the door from being closed if the part is not properly set in the fixed position.

BACKGROUND OF THE INVENTION

There are a number of known types of infusion pumps including a peristaltic infusion pump with which infusion is accomplished by successively pressing an infusion tube with fingers, a roller type infusion pump with which infusion is accomplished by pressing an infusion tube with a disk provided with a rotary roller, and a syringe type infusion pump with which infusion is accomplished by pressing the piston of a syringe.

Out of these different types of infusion pumps, in the peristaltic infusion pump so configured as to accomplish infusion by successively pressing its infusion tube with fingers, after a door is opened, a midway part of the detachable infusion tube is temporarily held in a groove which is to serve as the fixed position of this part on the infusion pump body side, the door is closed and fixed to the pump body, the infusion tube is fully held by placing it in a state of being interposed between a plurality of fingers which are individually driven on the outer circumferential face of an infusion tube by a pumping mechanism built into the pump body and a bearing plate with an energizing function provided on the door, and infusion is carried out by pressing the outer circumferential face with the plurality of fingers along with the driving of the pump mechanism.

SUMMARY OF THE INVENTION

The peristaltic infusion pump configured as described above is readied for use in infusion when, after holding the midway part of the detachable infusion tube in the groove which is to serve as the fixed position of this part on the infusion pump body side, the door is closed.

More specifically, the upstream side of the infusion tube is set in the groove in the pump body and passed over the plurality of fingers of the pump mechanism, and the downstream side is temporarily set in a tube clamp. In this temporary setting, even if the infusion tube is not properly passed over the plurality of fingers of the pump mechanism, the door may be closed because the tube is soft enough to allow that. Especially when someone else than a nurse, such as the patient himself or herself or one of his or her family members, handles the pump, the door is more likely to be closed with the infusion tube pinched in-between. It is necessary to anticipate such a dangerous case in order to prevent accidents that could otherwise be avoided.

As the door is mounted with various functional parts which add to its weight, simple pivoting of the door on the pump body to make possible its easy opening and closing might entail the operational inconvenience of letting the door automatically close by its own weight.

The present invention, attempted in view of these problems, is intended to provide an infusion pump having a function to prevent its door from closing or being closed if, after the door is opened and a midway part of an infusion tube is temporarily held in its fixed position on the pump body, the infusion tube is not properly set in its fixed position.

The invention is also intended to provide an infusion pump improved in operational convenience for the opening and closing of its door to be provided on the pump body to be readily opened or closed.

Other features and advantages of the present invention will be apparent from the following description taken in conjunction with the accompanying drawings, in which like reference characters designate the same name or similar parts throughout the figures thereof.

BRIEF DESCRIPTION OF THE DRAWINGS

FIG. 9A through FIG. 9C are sectional views along the Y—Y line in FIG. 3, FIG. 9A showing a state in which the door is opened, the infusion tube 2 is set, and the door is closed; FIG. 9B showing a state immediately before the door is closed after a midway part of the infusion tube 2 is properly held temporarily in its fixed position on the pump body; and FIG. 9C showing a state in which the door is fully closed and locked.

DETAILED DESCRIPTION OF THE PREFERRED EMBODIMENTS

A preferred embodiment of the present invention will be described in detail with reference to accompanying drawings. The following description presupposes a peristaltic finger system the present applicant proposed in Japanese Patent Laid-Open No. 9-151856, in which, while fingers fully squeeze the infusion tube in a blocked state only on the upstream and downstream sides, the midway part between the blocked positions is not fully squeezed, resulting in a highly accurate infusion system immune from the influence of the wall thickness of the infusion tube. This embodiment is not only applicable to this system but also adaptable to an infusion pump of a peristaltic finger system, in which it is made possible to let the infusion tube function peristaltically by fully squeezing it.

Figure 1:
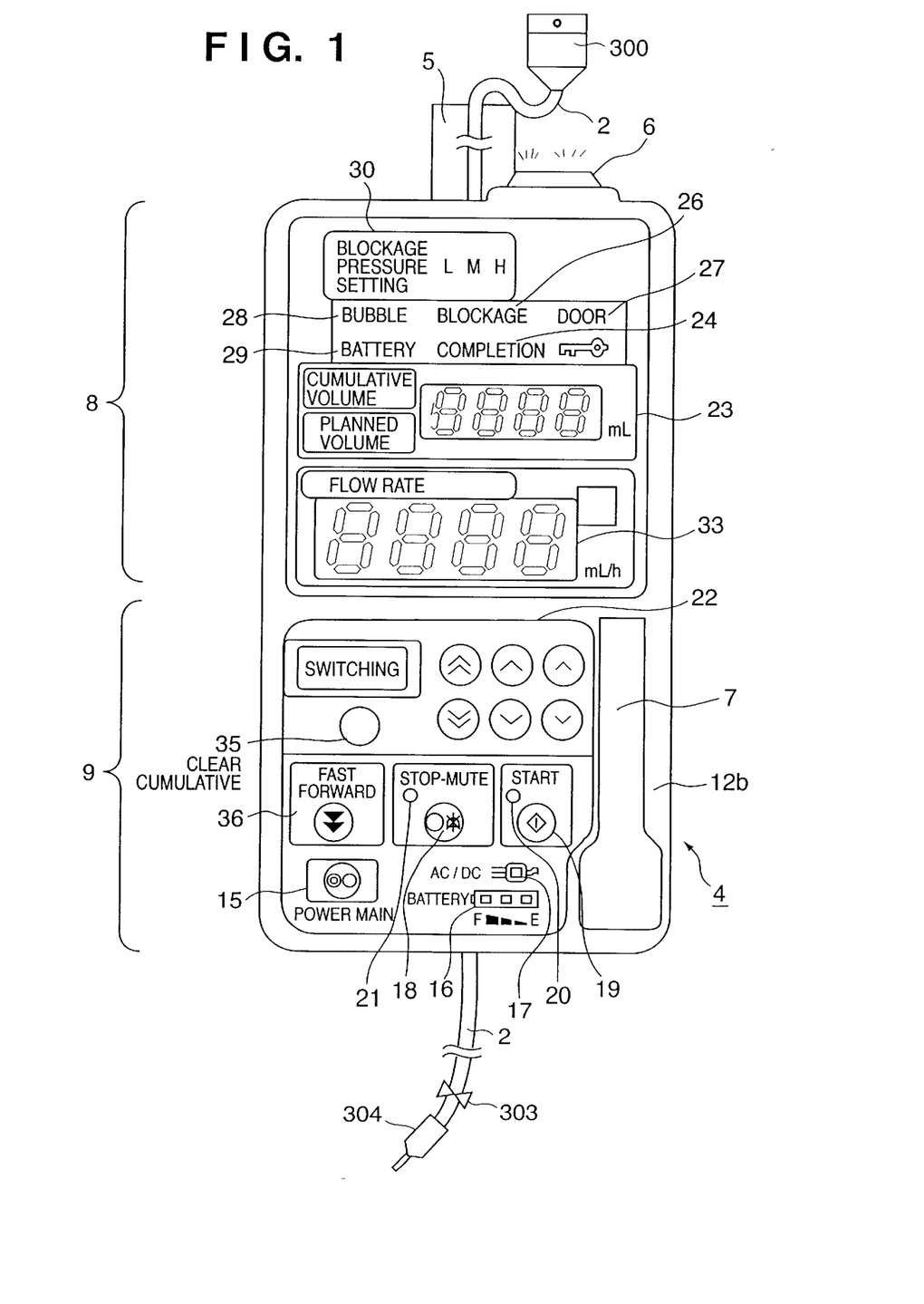
FIG. 1 is a front view of an operation switch panel provided on the front side of a fusion pump 1.

First, FIG. 1 shows a front view of an operation switch panel provided on the front side of an infusion pump 1.

Referring to FIG. 1, an infusion bag 300 containing a prescribed medical fluid is connected to the upstream side of an infusion tube 2; a midway part of the infusion tube 2 is set into the infusion pump 1 as illustrated; and an intravenous needle 304 is also provided, which is connected via a clamp 303 farther down stream on the infusion tube 2. By thrusting this intravenous needle 304 into a vein of a patient, the medical fluid is injected.

For this operation, the infusion bag 300 is hung on a stand pole (not shown) to make possible more precise infusion into the patient lying on a bed.

FIG. 1 illustrates a state in which, after temporarily setting the midway part of the infusion tube 2 as illustrated, a door base 4 is closed, and the infusion pump 1 is readied for starting infusion by operating a door lock lever 7. In this display section, every unit in the so-called seven-segment numeral display parts is "8". This indicates that a numerical value, an error or "–" to be displayed in each of these parts.

While the base of the pump body illustrated in this drawing, both serving as the base of the body of the infusion pump 1 and constituting the contour shaping part of the body is made of either aluminum die cast or rigid resin to ensure required strength and precision, operating switches and the display section are provided on the door base 4, which can be opened and closed pivoting on the left edge of this body base.

Thus a key panel section 9, on which operating switches are arranged, and a display section 8 are arranged, broadly distinguished from each other by frame printing. These key panel section 9 and display section 8 consist of transparent resin films, adhered so as to cover the keys (not shown), on whose back side prescribed items are printed and embossed to swell out to the front side in a round shape. This film covering prevents the medical fluid or the like from infiltrating into the inside of the pump.

The switch keys are mounted on a common substrate, and LEDs on the display section 8 make the display readily recognizable even at night. The switch keys, display units and lamps are connected by flexible cables to a control unit to be described later, and power supply and drive signals are transmitted via these cables. The configuration is such that power can be supplied, and drive signals conveyed, as the door base 4 provided with a door face cover is opened or closed. These key panel section 9 and display section 8 provided on the door base 4 are intended to handle electric signals of a TTL level alone.

Next to describe the function of each switch, a power switch 15 arranged in the bottom left corner of the drawing is used for turning on and off the main power supply. Keeping this switch for a prescribed number of seconds (about 2 seconds or longer) turns the power supply on, and again keeping it pressed for another prescribed number of seconds (about 3 seconds or longer) turns it off, so that the power supply cannot be turned either on or off inadvertently. A battery lamp set 16 to the right of the power switch 15 has green light emitting diodes (LEDs) with a three-level indicating capability as illustrated. Irrespective of whether the main power supply is on or off, one of the battery lamps is on whenever an A.C. power source or a dedicated D.C. power source is connected, so that it can be indicated that the battery is being charged. The three-level LED displaying arrangement indicates the level of charge or that of the remaining power when the built-in battery is being charged or consumed.

Above this battery lamp set 16 is an A.C./D.C. lamp 17 which is continuously on only when a commercial power source or a D.C. power source is being used and the power supply is on.

Still above this lamp, there is a stop-mute switch 18, which, when pressed during infusion, actuates a built-in buzzer and forcibly stops infusion. If pressed when the alarm is sounding, this stop-mute switch 18 will mute the alarm or, if kept being pressed for a prescribed number of seconds (about 2 seconds or longer) in a state in which the pump is ready to start infusion, will set the pump in a "stand-by mode" to release the pump from an alarmed state to urge the operator not to forget starting. Therefore, when for instance a surgery team is standing by in an operating room with the needle already thrust into the patient's vein, the alarm can be prevented from sounding before infusion is started. To the left of this stop-mute switch 18 is a stop indicator lamp 21 consisting of a diode which is lit in amber when infusion is at halt. This lamp is associated with the stop-mute switch 18 by encircling it in the same frame.

To the right of this stop-mute switch 18 is a start switch 19. When the start switch 19 is pressed, a buzzer built into it sounds, infusion is started, and the active state is indicated by intermittent light of a green LED constituting a start indicator lamp 20. To the left of the stop-mute switch 18 is a fast forward switch 36. By keeping this switch pressed, the fluid can be infused faster than the set speed (in mL/h) as long as it is pressed.

Above these switches, a total of six up/down switches 22 are arranged as illustrated, which are setting means respectively matching displayed digits in a planned flow rate display section 33 located in the lower part of the encircled display section 8. By pressing, when the pump is not on, the up or down button matching the pertinent digit of the up/down switches 22, the flow rate and the planned rate can be set. By pressing an up/down switch 22 then, the reading of the rate varies by 0.1 mL/h or 1 mL/h a time, and it is so programmed that the flow rate range can be set between the minimum of 1.0 and the maximum of 500 mL/h.

Above this planned flow rate display section 33 is arranged a cumulative volume/planned volume display section 23 encircled in another printed frame. The planned volume can also be set within a range of 1 to 9999 mL by pressing the up or down button matching the pertinent digit of the up/down switches 22. It is programmed to permit choice between setting in 1 mL units or free-hand setting, and the set volume is stored in either case.

It is further programmed to indicate the cumulative volume of infusion in either 0.1 mL or 1 mL units within a range of 0.0 to 9999 mL. As both the flow rate display section 33 and the cumulative volume/planned volume display section 23 use LEDs for displaying, their readings can be seen at night and in a dark room without special illumination.

Above the cumulative volume/planned volume display section 23 is arranged an alarm display section having various alarm characters encircled in another printed frame as illustrated. In this alarm display section, there are provided, again encircled in another printed frame, a completion display section 24 where characters indicating "completion" are intermittently lit; an abnormal blockage display section 26 where characters indicating "blockage" are intermittently lit to urge a remedial action when any abnormal blockage of the infusion tube 2 is detected and normal infusion is impossible; a door open display section 27 where characters indicating "door" are intermittently lit when an incomplete state of the closing of the door base 4 against the pump body base 3 is detected by a door switch; an abnormal bubble display section 28 where characters indicating "bubble" are intermittently lit when any bubble of a prescribed length (10 mm) or longer has entered into the infusion tube 2; and a battery abnormality display section 29 where characters indicating "battery" are intermittently lit when the voltage of the built-in battery has dropped.

To the left above this alarm display section is provided an occlusion pressure setting display section 30 consisting of LEDs indicating in green the level of occlusion detection alarm pressure in the infusion tube 2 constantly at one of three levels including "H" (high), "M" (middle) and "L" (low), arranged from left to right as illustrated. The lit LED indicates the preset level of occlusion detection alarm pressure. These LEDs are mounted on the same packaging substrate, and receive power supply from the aforementioned flexible cables.

The door base 4, made of either aluminum die cast or rigid resin, has its curved face, which constitutes a key design factor, between its side and front faces, and is provided with an action indicator 6 formed protruding from its top face. LEDs emitting red and green lights are built into this action indicator 6, and are lit according to the action that is taking place. Thus, they are lit intermittently when the fluid is infused either at the regular speed or fast forward, or the red and the green are alternately lit when the stand-by function is at work so that it can be known that infusion can be started at any time.

Figure 2:
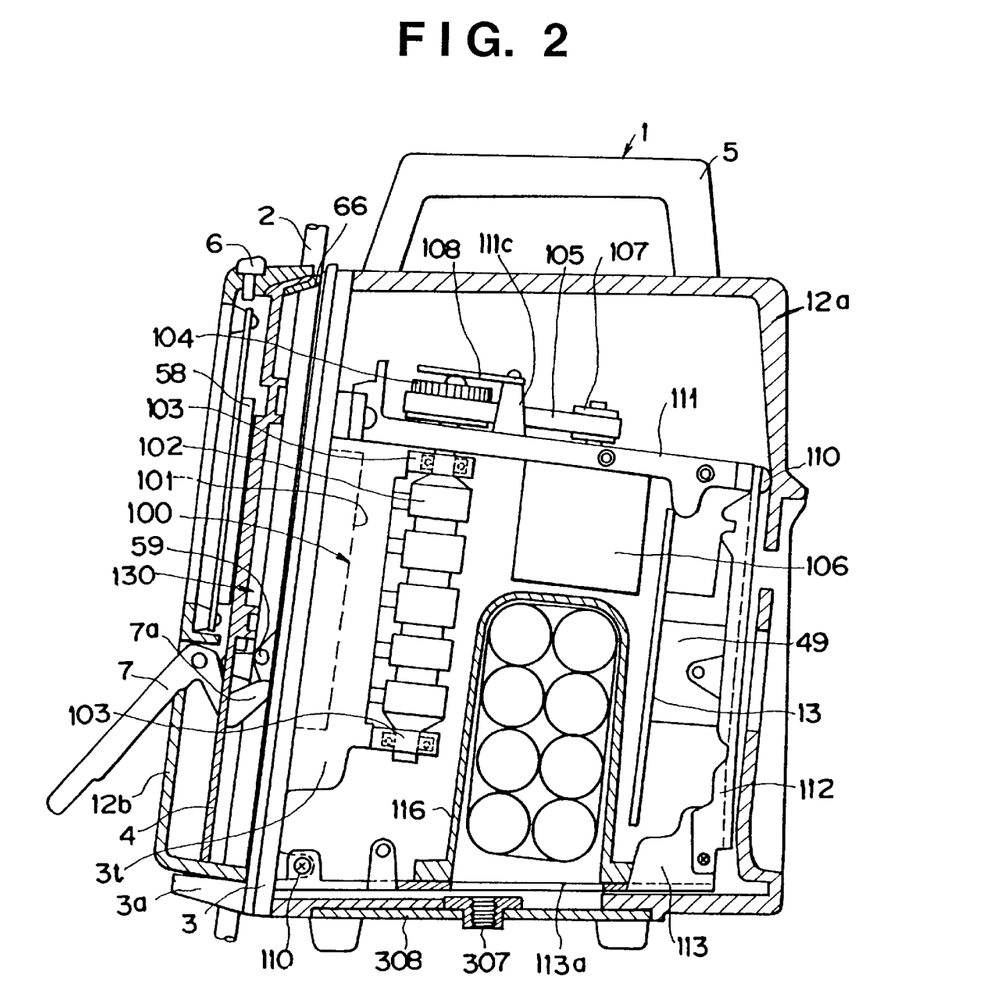
FIG. 2 is a cross-sectional view of the infusion pump 1.

Next, FIG. 2 is a cross-sectional view of the infusion pump. Constituent parts already described and again shown in this drawing will be assigned respectively the same reference signs, and their further description will be dispensed with. Referring to FIG. 2 in addition to FIG. 1, the infusion pump 1 is so fixed that the four corners of the pump body base 3 are covered by a body face cover 12a formed of a prescribed kind of resin material by special injection molding not to leave any shrinkage or track of resin overflow. By removing this body face cover 12a, every position within the pump can be easily accessed. This means a design intended for facile maintenance and reassembling. At the top of this body face cover 12a is provided a handle 5 for carrying convenience, formed integrally with the body face cover 12a.

Behind this infusion pump 1 are arranged, mounted on a back side substrate 13 indicated by the broken line in FIG. 2, an external communication connector, a fuse holder (neither shown) and an A.C. power supply connector (receptacle) 49 and a history switch and a D.C. connector, both mounted on a main packaging substrate (not shown), all so configured as to protrude outside through an opening.

Figure 3:
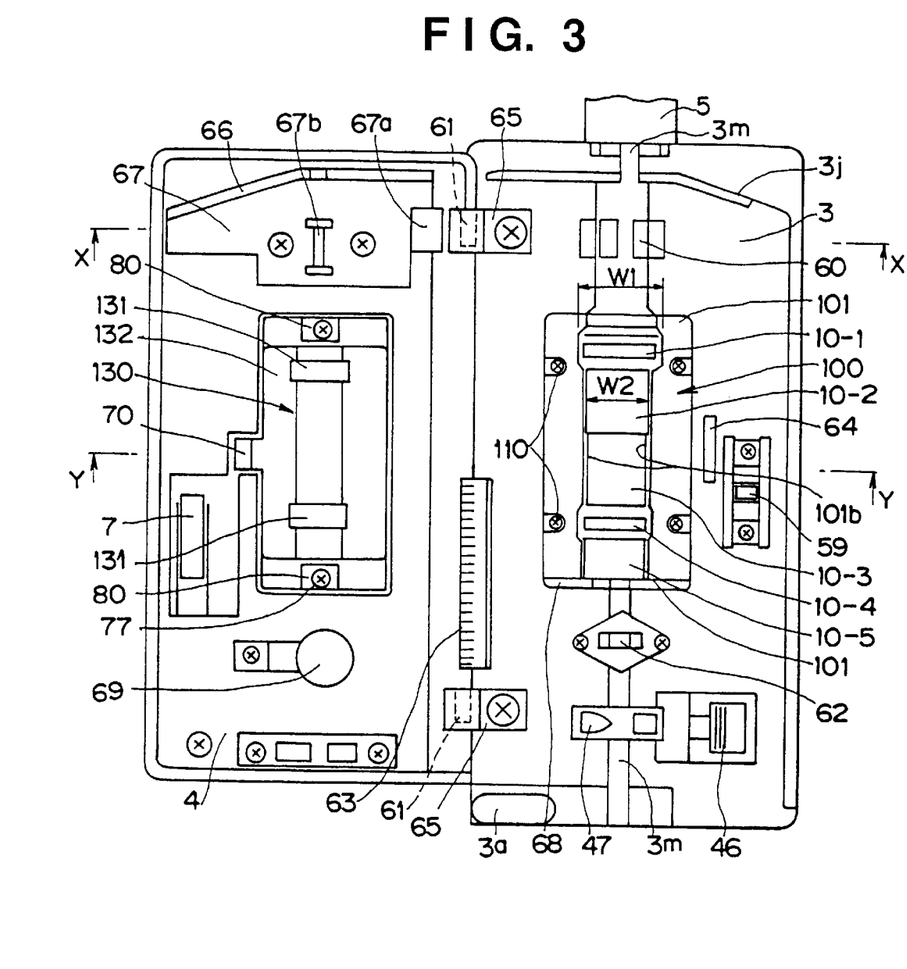
FIG. 3 is a front view of the infusion pump 1 before the loading of an infusion tube 2, with a door base 4 open.

Next, FIG. 3 shows a front view of the infusion pump 1 before the loading of the infusion tube 2, with the door base 4 open. Whereas the door base 4 is shown in a state in which it is open to substantially the same plane as the pump body base 3 for the convenience of description, the door base 4 stops when it is opened to a prescribed angle, i.e. approximately 105 degrees, as will be described later.

Referring to FIG. 3, a groove 3m is formed about in the middle of and integrally with the pump body base 3 in the vertical direction, and the configuration is such that infusion tube 2 is set within this groove 3m. In approximately the middle of this groove 3m, there is provided a pump mechanism 100 detachable by removing a total of four screws 110 with a Phillips head screwdriver. This pump mechanism 100 is so designed, when it is contaminated with the medical fluid or the like and the moves of fingers 10-n have become unsmooth, the pump mechanism 100 can be taken out of the pump body base 3 and cleaned with a prescribed detergent to wash off the contaminant and to enable the fingers to move normally again. In this connection, the fingers 10-1, 10-2, 10-3, 10-4 and 10-5 provided on the pump mechanism 100 are extrusion-molded of a thermoplastic resin material highly resistant to chemicals, such as polyacetal resin.

In the lower part of the pump body base 3, a pair of protruding jaws 3a are integrally formed to hold the groove 3m between them. When the door base 4 provided with a door face cover 12b shown in FIG. 2 is closed, the lower sides of the door face cover 12b are positioned over these protruding jaws 3a, which would intercept any external impact and prevent it from affecting the door face cover 12b and the door base 4.

In the lower part of the groove 3m is arranged a tube clamp 47 to automatically press and hold the infusion tube 2 temporarily when the door base 4 is opened, and the tube can be released from the pressure as desired with a release lever 46 adjoining the clamp on the right. The release lever 46, which is operated by pressing, is also designed to release, when it is pressed, the infusion tube 2 from the clamping by the clamp 47. Therefore, it is used when the tube is to be released from the clamping by the tube clamp 47, and an infusion set is to be fitted or removed. Further, in the middle right side part of the pump body base 3 is fixed a hook 59, and engagement of an engaging part 7a of the door lock lever 7 provided rotatably on the door base 4 with this hook 59 makes possible operation of the door to maintain the state of its being fixed to the pump body.

On the door base 4 side, opposite the farthest upstream part of the groove 3m, there is arranged a door seal rubber 66 consisting of an elastomer. When the door base 4 is closed, the pump body base 3 is preventing from letting the medical fluid come in by causing the door seal rubber 66 to be deformed so as to form a junction sealing face between it and a shape 3j, which is illustrated. The door seal rubber 66 is fixed and prevented from falling off by a tube keeping plate 67 fixed to the door base 4.

Underneath the shape 3j is arranged a bubble sensor 60. This bubble sensor 60 is intended to forcibly stop, when any one of a prescribed length (e.g. about 10 mm) which would mean a prescribed volume (about 0.08 cc) or more is detected out of bubbles coming into the infusion tube 2, any subsequent action, and in the position on the door base 4 side opposite this bubble sensor 60 is formed the tube keeping section 67b integrally with the tube keeping plate 67 so that, when the door base 4 is closed, accurate bubble detection can be accomplished by keeping the infusion tube 2 immovable.

Underneath this bubble sensor 60 is positioned the pump mechanism 100, and farther underneath is arranged an occlusion sensor 62. Together with a blockage keeping plate 69 arranged on the door base 4 to be opposite to it, the occlusion sensor 62 holds the infusion tube 2 in the forward and backward directions of the drawing sheet. This occlusion sensor 62, consisting of a permanent magnet and a pickup for detecting in an analog manner the shifted position of this permanent magnet, detects the position of the permanent magnet shifting with a variation in internal pressure accompanying the blocked state of the infusion tube 2. Since this means that it is required to prevent the blockage keeping plate 69 from regulating internal pressure variation in the infusion tube 2 in all directions, the disk illustrated in the drawing is held movably at the end of a spring plate (elastic member).

On the other hand, the operating principle of the pump mechanism 100 is such that infusion is continuously carried out at a set flow rate per unit time by pressing the fitted infusion tube 2 with the fingers 10-1, 10-2, 10-3, 10-4 and 10-5. A motor revolution signal is generated according to information stored in a microcomputer (CPU), the motor is turned according to this revolution signal, the pump is driven, and the flow rate of infusion is controlled accordingly.

The fingers 10-1, 10-2, 10-3, 10-4 and 10-5 are built in so that each of the first finger, second finger, third finger, fourth finger and fifth finger from the upstream downward is driven reciprocatively in the forward and backward directions of the drawing sheet within a pump base 101 as illustrated. As shown in the drawing, the first finger 10-1 and the fourth finger 10-4 are shaped different from the other second finger, third finger and fifth finger. Thus, the width W1 of the first finger and fourth finger is greater than the width W2 of the other fingers. Also, the pressing faces of the first finger and the fourth finger have convex parts.

Thus, the differentiated shapes of the fingers enable the aforementioned peristaltic finger system proposed by the applicant in Japanese Patent Laid-Open No. 9-151856 to function ideally.

Thus, the convex parts formed on the pressing faces of the first finger 10-1 and the fourth finger 10-4 fully block the infusion tube 2 only on the upstream and downstream sides, but the other second finger and third finger do not fully squeeze the midway part, resulting in highly accurate infusion immune from the influence of the wall thickness of the infusion tube. As the first finger and fourth finger, when they fully squeeze the infusion tube 2, cause the infusion tube 2 to expand laterally, the width W1 of the first finger and fourth finger is made greater than the width W2 of the other fingers. To add, the fifth finger 10-5 is intended for compensating for pulsation.

Furthermore, in a conventional peristaltic system, all the fingers 10-n are made similar to the second finger 10-2 to fully squeeze the infusion tube 2, which is thereby enabled to move peristaltically.

Next, the door base 4 is configured to open leftward in relation to the pump body base 3 pivoting on a pair of hinge blocks 65, upper and lower, and pins 61 indicated by the broken lines in the drawing. Power supply to the display section 8, key panel section 9 and action indicator 6 is accomplished via a flexible cable 63 which is resistant to repeated bending. In about the middle part of this door base 4 is arranged a back plate mechanism 130 opposite the pump mechanism 100.

The back plate mechanism 130, which serves as a pad, is formed as a surface to bear the pressures form the fingers by being arranged opposite the fingers 10-n of the pump mechanism 100. It is movable in the forward and backward directions of the drawing sheet, and has a function to retreat, if any overload arises, toward the back side of the sheet to prevent the infusion tube 2 from being damaged. As the first finger 10-1 and the fourth finger 10-4 fully squeeze the infusion tube 2, back plate members 131 are provided opposite these fingers separately from the back plate base 132 to be movable in the forward and backward directions of the drawing sheet.

Referring again to FIG. 2, in the pump body base 3, shapes 3t to detachably accommodate the pump mechanism 100 indicated by the broken line in the drawing are formed integrally with the jaws 3a. These jaws 3a are formed at the same level as or slightly higher than the door base 4, and protect the door base. The pump body base 3 serves as the fitting base of various members, and constitutes the upper surface frame part of the pump system by fixing an upper plate 111, which is an aluminum die cast upper plate member, as illustrated. On the back side of this upper plate 111, a back side plate 112 fabricated from a steel plate of 1 to 2 mm in thickness is fixed with two screws 110 in fitting parts of the upper plate 111, where tapped holes are provided, to constitute a back side frame part behind the pump system. Between the lower part of the pump body base 3 and the back side plate 112, a lower plate 113 is fixed with screws 110 to constitute a bottom frame part of the pump system. Thus is formed a body frame of a sturdy closed structure by the pump body base 3, upper plate 111, back side plate 112 and lower plate 113. It may as well be formed of the upper plate 111, back side plate 112, lower plate 113 and battery case 116 molded integrally.

Thus the configuration embodies an intention to secure sufficient rigidity, protect the mechanism, circuit board and other components even if the assembly is dropped by mistake and to minimize any possible effect of electromagnetic waves by either encircling the mechanism and the substrate to be built in with upper, lower and back side plates of a sufficiently strong pump body base 3 or integrating them altogether.

In the upper and lower positions of the shapes 3t of the pump body base 3 are fixed bearing blocks 103 with built-in bearings for rotatably supporting a camshaft 102. To a shaft at the upper end of this camshaft 102 is fixed a toothed pulley 104 with screws (not shown). To the upper plate 111 is fixed a stepping motor 106, at its output shaft, a toothed pulley 107 whose diameter is not greater than the toothed pulley 104 with screws (not shown), and a toothed belt 105 spanning the two pulleys transmit the rotational force of the stepping motor 106 to the camshaft 102. Each pulley is flanged at only one end as illustrated, so that the toothed belt 105 can be fitted or replaced without removing the stepping motor 106.

Furthermore, on the circumference of the camshaft 102, an eccentric cam shape equivalent to the fingers 10-n is integrally formed by machining with a computer-controlled device with sufficient precision ensured. As the camshaft 102 is highly precise, if an infusion tube with adequate dimensional precision is used, a flow rate tolerance can be guaranteed within 75%. This integrated camshaft 102 is made by machining a stainless steel material, such as SUS 304.

A revolution detecting sensor 108 detects the position and frequency of revolution of the camshaft 102 by optically reading a timing disk (not shown) fitted to an upper side face of the toothed pulley 104. To make this possible, the revolution detecting sensor 108 is fixed to a fitting part 111c integrally formed on the upper plate 111.

The above-described back side plate 112 is arranged behind the motor 106 as illustrated, and at the same time serves as the fitting base of the back side substrate 13 on which a power supply connector and other items are mounted. The battery unit 116 is so arranged underneath the motor 106 as to permit battery replacement through an opening 113a formed in the lower plate 113. For this reason, a back lid 308 to close the bottom of the body face cover 12a is screwed onto the lower plate 113. To this back lid 308 is fixed a fixed tapped hole member 307 for fixing the whole pump system to a stand.

The above-described pump mechanism 100 is so configured that, after it is fixed to the shapes 3t with four screws 110, small radial bearings 120 of the fingers, to be described later, come into contact with the cam face 102a of the camshaft 102. The upper plate 111 is so shaped as to stay away from the toothed pulley 104, and can be fixed in a state in which the camshaft is fixed. This arrangement to enable the upper plate 111 to be fixed in the assembling process even after the camshaft 102 is assembled is intended to avoid an uncoordinated assembling sequence. The battery unit 116, shaped as illustrated, is fixed to the lower plate 113. On the other hand, the flexible cable 63, extending from the main packaging substrate (not shown) 14, is so configured as to pass the opening in the pump body base 3 and to emerge as illustrated in FIG. 3.

The main packaging substrate, which stores a program to be described below and takes charge of prescribed controls, is provided with a plurality of connectors arranged upward, and configured to be screwed to fix its upper edges to side faces of the upper plate 111. This main packaging substrate is designed to be hardly susceptible to external noise by setting the grounding pattern widely and giving appropriate consideration to the mounting patterns of electronic parts, and accordingly can be effectively used in an operating room where a variety of noise emitting devices are used.

Figure 4:
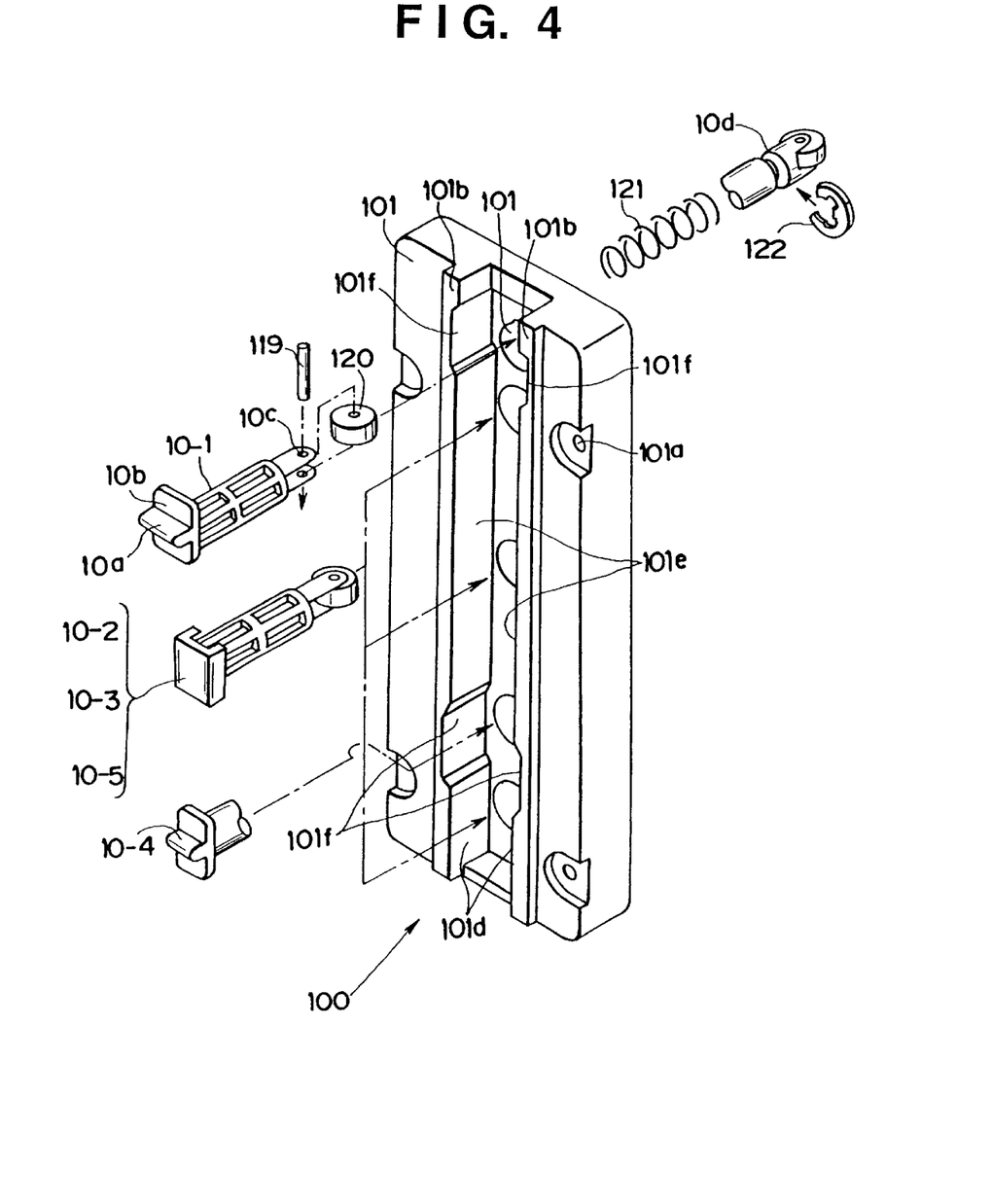
FIG. 4 is a three-dimensional exploded view of an infusion pump mechanism 100.

Next, FIG. 4 shows an external perspective view of a finger assembly constituting the pump mechanism 100. Referring to FIG. 4, the pump base 101 is made from a prescribed resin material of adequate resistance to chemicals by integral molding into the illustrated shape. Five guide holes 101c pierce this pump base 101 as illustrated, and the fingers, each fitted in advance with a small bearing 120 rotatably pivoting on a pin 119 fitted into a finger hole 10c, are charged into these guide holes 101c. These fingers are readied as the aforementioned first finger 10-1, second finger 10-2, third finger 10-3, fourth finger 10-4 and fifth finger 10-5 in the order from the upstream downward. When the fingers are charged, since the first finger 10-1 and the fourth finger 10-4 are shaped differently from the other fingers on account of the need to form a convex part 10a on the upper face 10b of each, they can be fitted to the pump base 101 without mismatching.

After the fingers have been charged into the pump base 101 as described above, each finger is shifted toward the aforementioned camshaft 102 by charging a compressed coil spring 121, which is an energizing member for each finger, and setting a retaining ring 122 in a groove 10d in the direction of the corresponding arrow.

Meanwhile, on the pump base 101, crests 101b formed on both right and left sides continuously from frictional contact faces 101d of the fingers as illustrated are integrally formed, and the back plate base 132 of the back plate mechanism 130 holds the infusion tube 2 in a state of keeping it in contact with these crests 101b. Finger guides 101f matching first finger 10-1 and the fourth finger 10-4 are set wider than other finger guides 101e.

Figure 5:
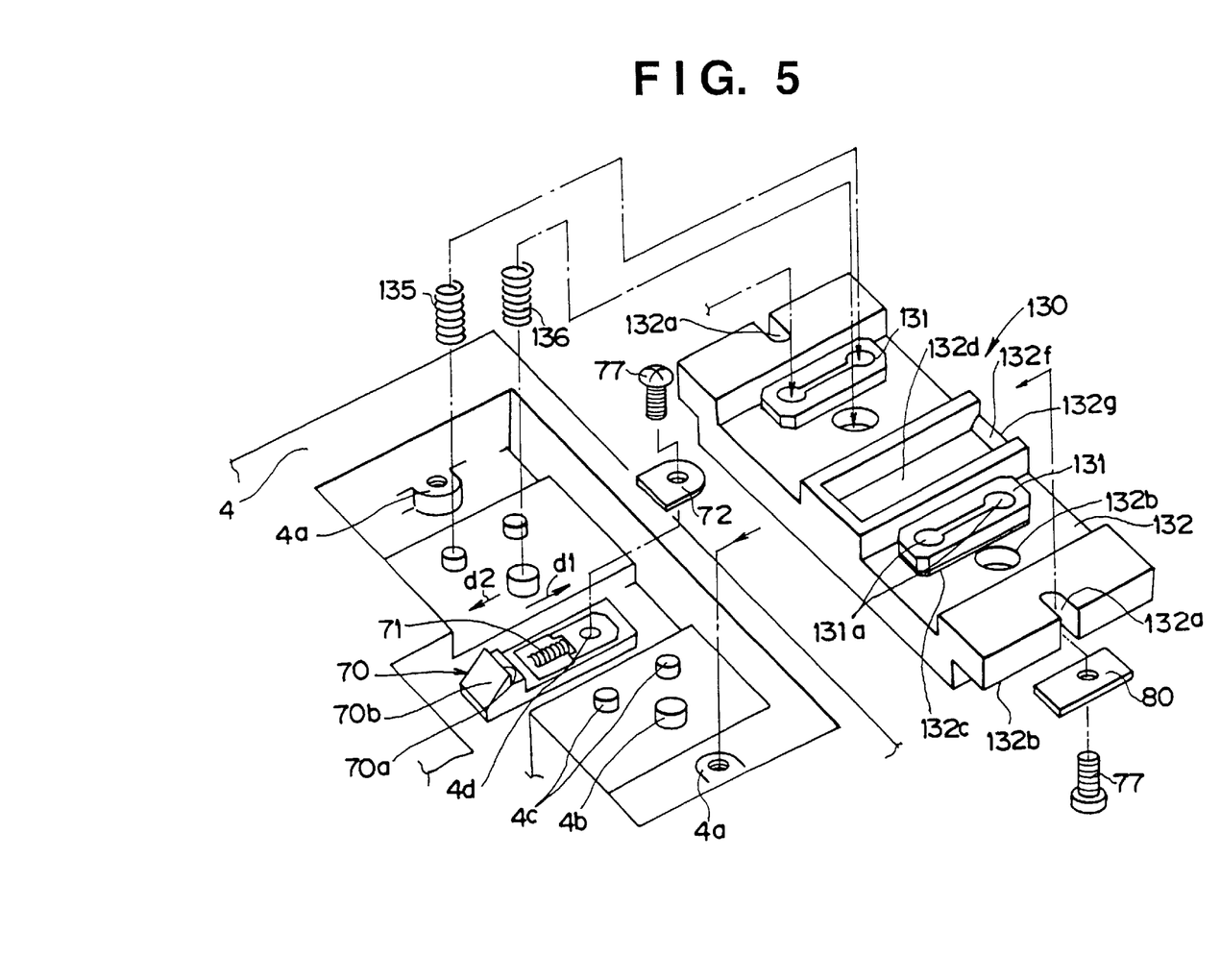
FIG. 5 is a three-dimensional exploded view of a back plate mechanism 130.

Next, FIG. 5 shows a three-dimensional exploded view of the back plate mechanism 130 inverted with respect to the door base 4. Referring to FIG. 5, the back plate base 132 is made from a prescribed resin material of adequate resistance to chemicals by integral molding into the illustrated shape. Crests 132b of this back plate base 132 are formed into a positional relationship of sneaking into the gaps between the crests 101b of the pump base 101 shown in FIG. 3, so that the same peristaltic motion can be transmitted to the infusion tube 2 all the time.

In this back plate base 132, which sets from behind the back plate members 131 provided opposite the first finger 10-1 and the fourth finger 10-4 as illustrated, holes 132a of the flanges of the back plate members 131 are integrally formed in mutually symmetric positions.

On the other hand in the door base 4, a stopper member 70 is provided to be movable in the direction of the corresponding arrow in a concave part as illustrated, and convex parts 4c and 4b to fix a pair of threaded parts 4a and large and small compressed springs (i.e. first and second energizing members) for fixing the back plate base 132 are integrally formed.

In order to provide the stopper member 70 to be constantly shiftable in the direction of the arrow d2 in the drawing, the convex part 4d centering on a tapped hole is provided on the door base 4 and, after bringing one of compressed springs 71 into contact with this convex part 4d and the other into contact with the inner wall of the opening in the stopper member 70, a bracket 72 is fixed to the convex part 4d with a screw 77.

In order to fix the back plate 132 to the above-described door base 4, first four small compressed coil springs 135 (first energizing members) are set to four convex part 4c and two large compressed coil springs 136 (second energizing members) are set to the convex parts 4b. After the small compressed coil springs 135 are set to enter into bottomed holes 131b of the back plate members 131 and to enter the large compressed coil springs 136 into the bottomed holes 132b, a pair of brackets 80 are fixed to a pair of threaded parts 4a with screws 77.

Further on the stopper member 70 are integrally formed an inclined face 70b which generates a component of shifting force in the direction of arrow d1 in the drawing by coming into frictional contact with an inclined face 132f formed on the back side of the back plate base 132 and an engaging part 70a which is brought into a state of engagement with a side wall part 132g of the back plate base 132.

This stopper member 70 is so configured that the coming into frictional contact of the inclined face 70b with a shape formed on the pump body base 3 when the door is closed causes a component of force to shift the stopper member 70 in the direction of the arrow d1 to be generated, and the generation of this force causes the engaging part 70a to be released from its state of engagement with the side wall part 132g of the back plate base 132.

Figure 6:
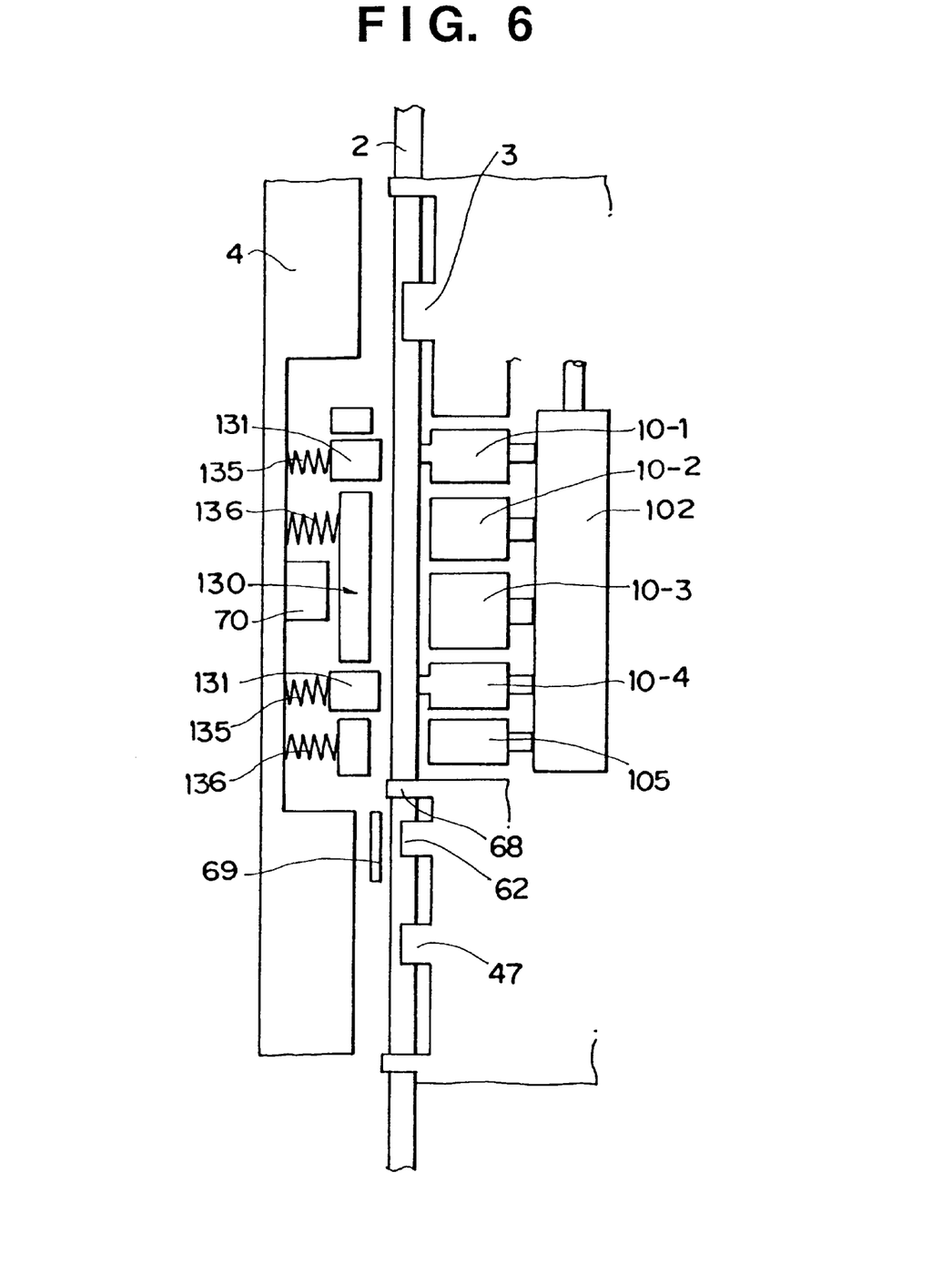
FIG. 6 illustrates a state in which the infusion tube 2 is interposed between the back plate mechanism 130 composed of a back plate base 132 and a stopper member and the pump mechanism.

In this manner, there arises the state of interposition, illustrated in FIG. 6, between the back plate mechanism 130, consisting of the back plate base 132 and the stopper member, and the pump mechanism. In this state, a relatively large and conspicuously colored tube holder 68 functions to hold the infusion tube in the downstream part of the pump mechanism.

Figure 7:
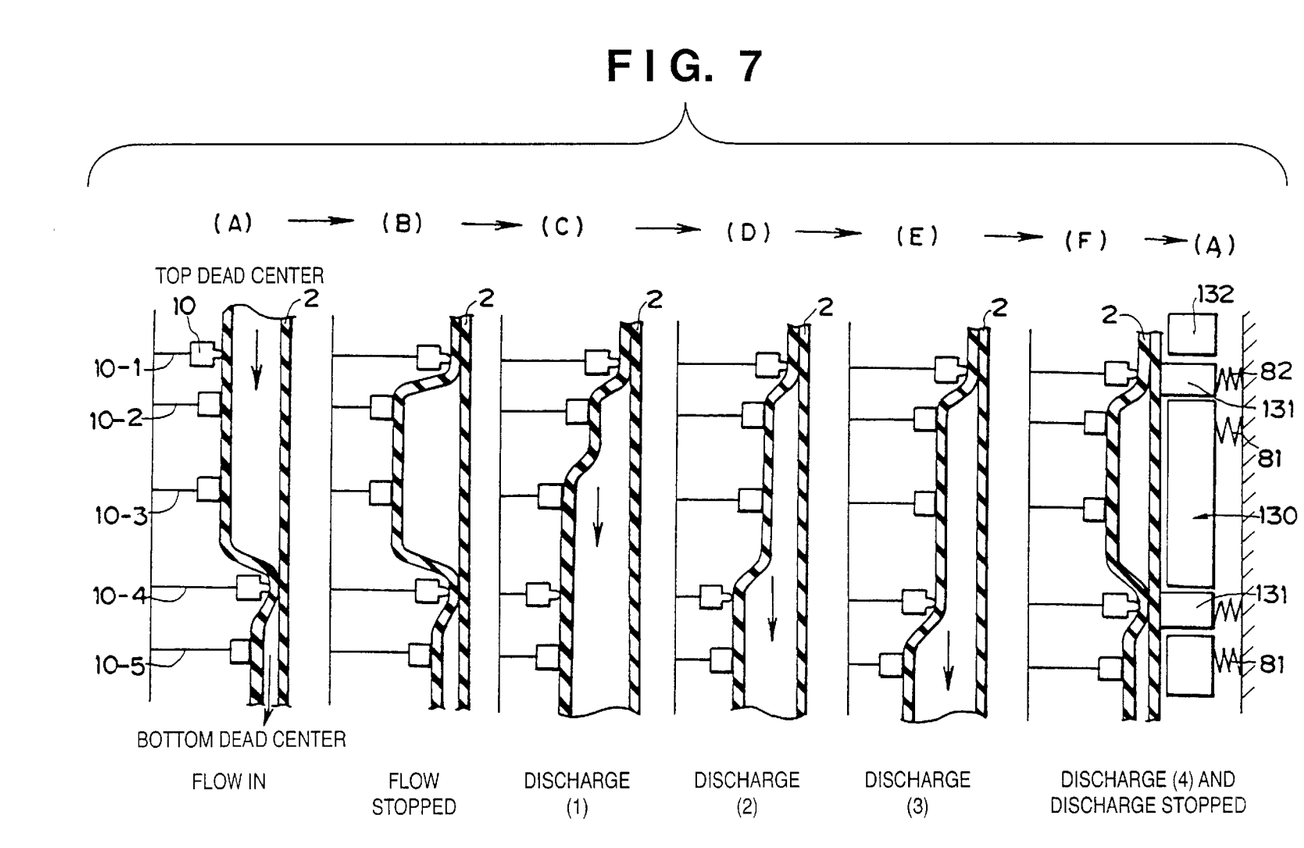
FIG. 7 illustrates how first through fifth fingers are operated.

Next, FIG. 7 is an operational diagram illustrating the relationship between the finger 10-n and the pressure-closed state of the infusion tube 2. Referring to FIG. 7, as infusion is begun by pressing the start switch 19 (see FIG. 1), the stepping motor 106, whose revolution is driven according to the flow rate setting, is actuated, and in state (A) a medicine fluid in its bag is let in by fully blocking the infusion tube 2 with only the fourth finger 10-4. Then, in state (B), the tube is fully blocked with the first finger 10-1 to lock in the medicine fluid between the upstream and downstream sides.

Then in state (C), the fourth finger 10-4 is withdrawn, and the fluid is delivered by pressing the infusion tube 2 to the midway with the second finger 10-2. Then in the following state (D), the fluid is delivered by pressing the infusion tube 2 to the midway by shifting the third finger 10-3. Then in the ensuing state (E), the fourth finger 10-4 begins to move for full blockage, and at the same time the fifth finger 10-5 begins to move quickly to lead to state (F). Repetition of the foregoing sequence of actions results in infusion by peristaltic motions without full squeezing. Here, the rapid start of action by the fifth finger 10-5 serves to bring pulsation, generated by the actions from state (A) through state (E) when a particularly high flow rate is set, close to a rectified flow. This series of pressing forces from the fingers are borne by the aforementioned back plate mechanism 130.

Figure 8A:
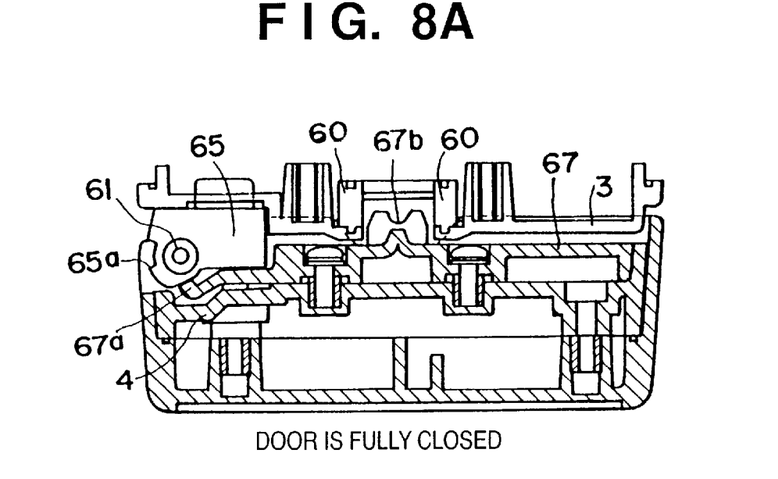
FIG. 8A and FIG. 8B are sectional views along the X—X line in FIG. 3, FIG. 8A showing a state in which the door is closed, and FIG. 8B, a state in which the door is opened to its limit.
Figure 8B:
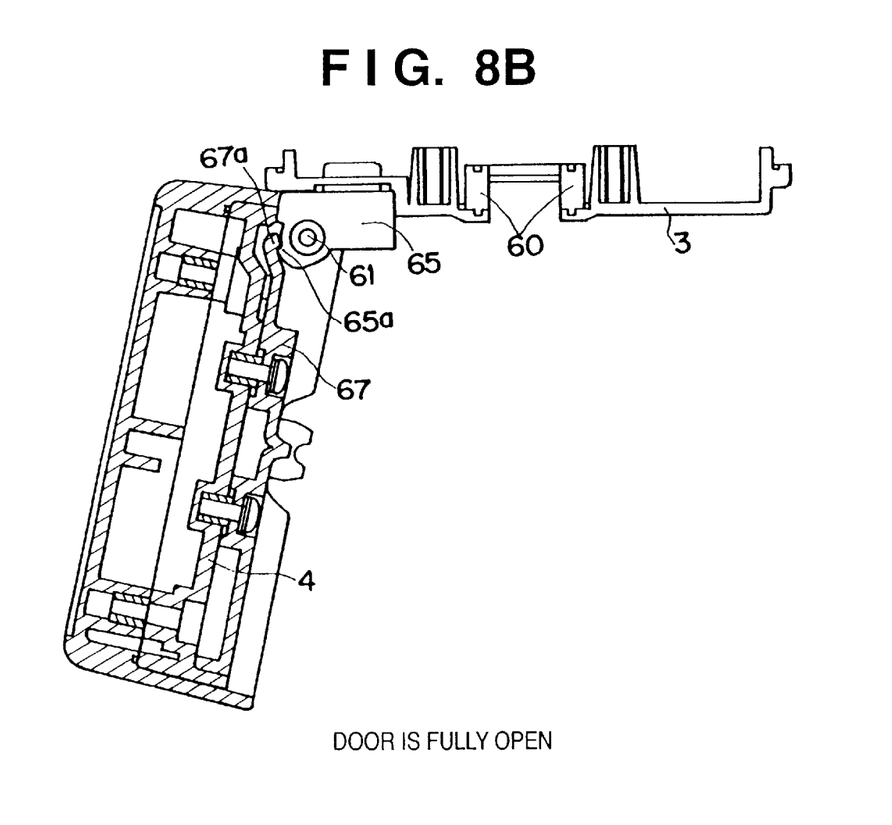

Next, FIG. 8A and FIG. 8B show sectional views along the X—X line in FIG. 3, FIG. 8A showing a state in which the door is closed, and FIG. 8B, a state in which the door is opened to its limit. Constituent parts already described and again shown in this drawing will be assigned respectively the same reference signs, and their further description will be dispensed with. An elastically deformable shape 67a is integrally formed with the tube keeping plate 67 fixed to the door base 4 with screws, and an end of this shape is kept constantly in contact with the outer circumferential face of the hinge block 65. At the terminal end of the outer circumferential face of the hinge block 65 is formed a level gap 65a and, when the door is open as shown in FIG. 8B, the shape 67a falls into this level gap 65a.

The above-described configuration, in contrast to a case in which a heavy door is simply pivoted to be opened away from and closed toward the pump body, can cause a proper braking force to be applied and the operator to sense a click when the shape 67a falls into the level gap 65a, resulting in a significant improvement in the operational convenience of door opening and closing.

Figure 9A:
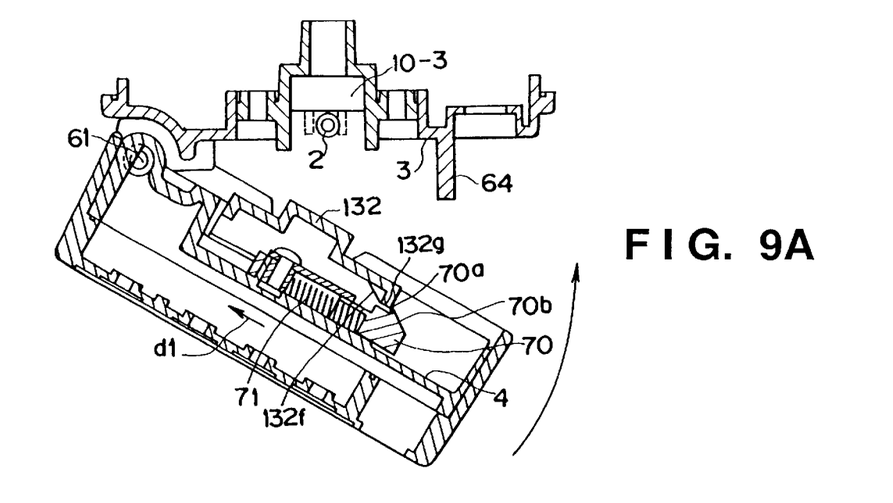
Figure 9B:
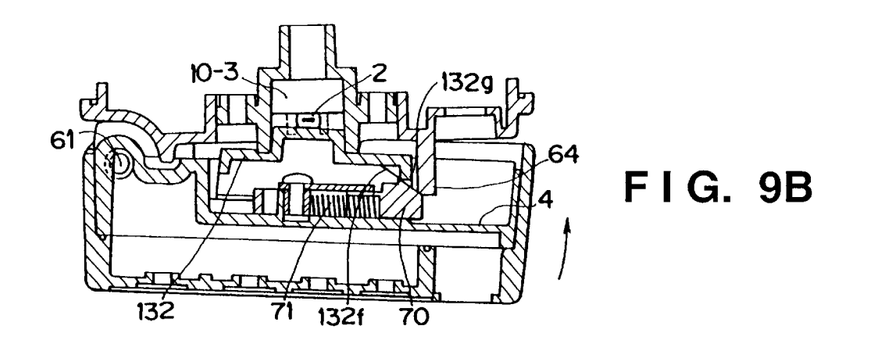
Figure 9C:
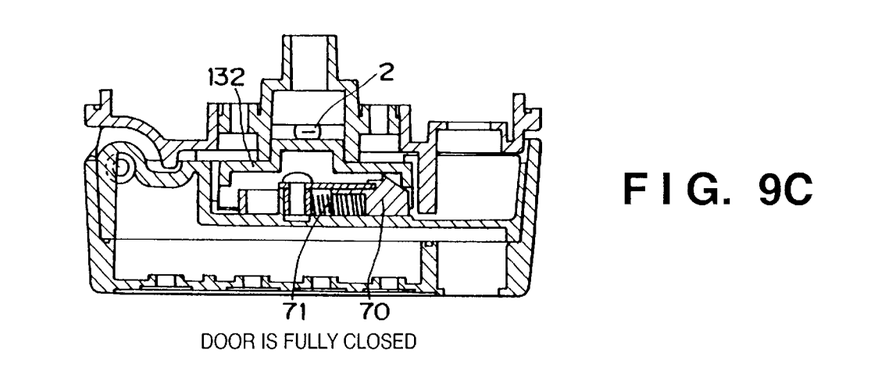

FIG. 9A through FIG. 9C show sectional views along the Y—Y line in FIG. 3, FIG. 9A showing a state in which the door is opened, the infusion tube 2 is set, and the door is closed; FIG. 9B showing a state immediately before the door is closed after a midway part of the infusion tube 2 is properly held temporarily in its fixed position on the pump body; and FIG. 9C showing a state in which the door is fully closed and locked.

Constituent parts already described and again shown in this drawing will be assigned respectively the same reference signs, and their further description will be dispensed with. Referring to FIG. 9A, on the pump body base 3, there is formed a shape 64 which, when the door is closed, generates a component of force to shift the stopper member 70 in the direction of arrow d1 in the drawing by coming into frictional contact with the inclined face 70b of the stopper member 70. In the illustrated state, the engaging part 70a of the stopper member 70 is in a state of engagement with the side wall part 132g of the back plate base 132.

As the door is closed from the state of FIG. 9A, the stopper member 70 is shifted further in the direction of arrow d1 in the drawing by being brought into frictional contact with the inclined face 132f formed on the back side of the back plate base 132. When the door is fully closed and locked, the engaging part 70a which has been in a state of engagement with the side wall part 132g of the back plate base 132 is contained within the back plate, and placed in a state of shifting along the inclined face, resulting in the realization of a normal function.

Figure 10:
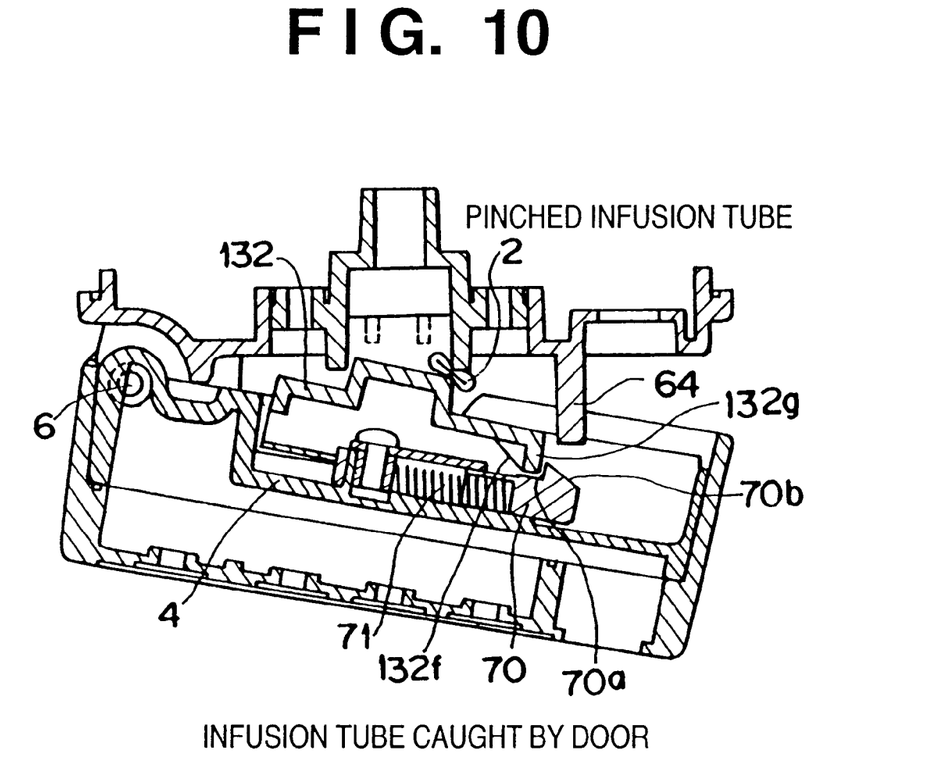
FIG. 10 is a sectional view along the Y—Y line in FIG. 3 in a state in which the midway part of the infusion tube 2 is not properly set.

On the other hand, as illustrated FIG. 10 which shows a sectional view along the Y—Y line in FIG. 3, if the midway part of the infusion tube 2 is not properly set, it is impossible to close the door to a position where the component of force to shift the stopper member 70 in the direction of arrow d1 is generated. As a result, the shape 64 cannot shift the stopper member 70, making it impossible to release the aforementioned state of engagement.

As stated above, when the upstream side of the infusion tube is set in the groove of the pump body and passed above the plurality of fingers of the pump mechanism and the downstream side is temporarily set to be held by the tube clamp, especially unless it is set to properly pass above the plurality of fingers of the pump mechanism, the door cannot be closed, resulting in the prevention of door closing with the infusion tube caught by the door.

As hitherto described, the present invention can provide an infusion pump having a function to actively prevent its door from being closed if, after the door is opened and the midway part of the infusion tube is temporarily held in its fixed position on the pump body, the infusion tube is not properly set in its fixed position.

In addition to the above-noted advantage, the invention can also provide an infusion pump improved in operational convenience for the opening and closing of its door to be provided on the pump body to be readily opened or closed.

Obviously, the invention is not limited to the above-described embodiment, but permits various configurations as defined in the appended claims.

What is claimed is:

1. An infusion pump, in which in order to temporarily hold a midway part of a detachable infusion tube in a fixed position of an infusion pump body and to place the tube in a state of interposition between a plurality of fingers which are individually driven on the outer circumferential face of the infusion tube by a pumping mechanism built into said pump body and a plate with an energizing function provided on a door pivoting on said pump body to be opened and closed, said door is fixed in relation to said pump body, and infusion is carried out by pressing said outer circumferential face with said plurality of fingers along with the driving of said pump mechanism, comprising:

a stopper member shifted by a shift energizing force to be placed in a state of engagement with said plate when said door is open in order to place said plate in said state of interposition and in an immovable state in relation to said door; and a shape provided on said pump body for shifting said stopper member against said shifting energizing force so as to release said state of engagement when the infusion tube is properly held temporarily in said fixed position and said door is shifted to a closed state in relation to said pump body.

2. The infusion pump according to claim 1, wherein said stopper member has an inclined face for generating a component of force for shifting the stopper member in said releasing direction by being in frictional contact with another inclined face formed on a back side of said plate and an engaging part to be placed in a state of engagement with a side wall part of said plate, said inclined face and said engaging part being integrally formed, and said shape generates a component of force for shifting said stopper member in said releasing direction by being in frictional contact with said inclined face.

3. The infusion pump according to claim 1, said infusion pump further comprising door stopper members which brake the opening/closing force of said door and hold the door at a substantially fixed angle in pivot sections to pivot said door for opening from and closing against said pump body.

4. The infusion pump according to claim 1, wherein, among the plurality of fingers of said pump mechanism, they being supposed to be a first finger, a second finger, . . . , and an Nth finger as counted from the upstream side to the downstream side of said infusion, said first finger and said Nth finger are individually driven to fully pressure-close said infusion tube and the other fingers and individually driven not to fully pressure-close said infusion tube, and said plate is provided with bearing members respectively matching said first finger and said Nth finger, said bearing members being energized by said energizing force of said plate.

* * * * *